(12) United States Patent
Pegington et al.

(10) Patent No.: US 9,859,499 B2
(45) Date of Patent: *Jan. 2, 2018

(54) POLYMER COMPRISING AN UNSYMMETRIC DIARYLAMINOFLUORENE UNIT

(71) Applicants: Sumitomo Chemical Company Limited, Tokyo (JP); Cambridge Display Technology Limited, Godmanchester (GB)

(72) Inventors: Ruth Pegington, Godmanchester (GB); Sophie Barbara Heidenhain, Lower Cambourne (GB); Mary J. McKiernan, Pangbourne (GB)

(73) Assignees: Sumitomo Chemical Company Limited, Tokyo (JP); Cambridge Display Technology Limited, Cambridgeshire (GB)

( * ) Notice: Subject to any disclaimer, the term of this patent is extended or adjusted under 35 U.S.C. 154(b) by 698 days.

This patent is subject to a terminal disclaimer.

(21) Appl. No.: 14/372,529

(22) PCT Filed: Jan. 16, 2013

(86) PCT No.: PCT/GB2013/050088
§ 371 (c)(1),
(2) Date: Jul. 16, 2014

(87) PCT Pub. No.: WO2013/108022
PCT Pub. Date: Jul. 25, 2013

(65) Prior Publication Data
US 2014/0353652 A1   Dec. 4, 2014

(30) Foreign Application Priority Data

Jan. 16, 2012 (GB) .................................. 1200619.3
May 16, 2012 (GB) .................................. 1208610.4

(51) Int. Cl.
| | | |
|---|---|---|
| C08G 61/12 | (2006.01) | |
| H01L 51/00 | (2006.01) | |
| C09K 11/06 | (2006.01) | |
| C07C 211/61 | (2006.01) | |
| C08G 73/02 | (2006.01) | |

(Continued)

(52) U.S. Cl.
CPC ........ *H01L 51/0043* (2013.01); *C07C 211/61* (2013.01); *C08G 61/12* (2013.01); *C08G 73/026* (2013.01); *C09K 11/06* (2013.01); *H01L 51/0039* (2013.01); *H01L 51/5056* (2013.01); *H01L 51/5203* (2013.01); *C07C 2603/18* (2017.05); *C08G 2261/135* (2013.01); *C08G 2261/148* (2013.01); *C08G 2261/1412* (2013.01); *C08G 2261/314* (2013.01); *C08G 2261/3142* (2013.01); *C08G 2261/3162* (2013.01); *C08G 2261/3245* (2013.01); *C08G 2261/411* (2013.01); *C08G 2261/512* (2013.01); *C08G 2261/76* (2013.01); *C08G 2261/95* (2013.01); *C09K 2211/1011* (2013.01); *C09K 2211/1014* (2013.01); *C09K 2211/1416* (2013.01); *C09K 2211/1433* (2013.01); *C09K 2211/185* (2013.01)

(58) Field of Classification Search
CPC ..................................................... C08G 61/12
See application file for complete search history.

(56) References Cited

U.S. PATENT DOCUMENTS

| | | | | |
|---|---|---|---|---|
| 8,993,124 B2 * | 3/2015 | Nakatani | ................. | C07C 25/22 257/40 |
| 9,267,003 B2 * | 2/2016 | Yoshida | ................. | C08L 79/02 |

(Continued)

FOREIGN PATENT DOCUMENTS

| | | |
|---|---|---|
| EP | 0 879 868 A2 | 11/1988 |
| EP | 0 879 868 A3 | 1/1999 |

(Continued)

OTHER PUBLICATIONS

International Search Report and Written Opinion for International Application No. PCT/GB2013/050088 dated Jun. 24, 2013.
International Preliminary Report on Patentability for International Application No. PCT/GB2013/050088 dated Jul. 31, 2014.
Office Communication dated Apr. 25, 2012 for Great Britain Application No. GB1200619.3.
Office Communication dated Aug. 20, 2012 for Great Britain Application No. GB1200619.3.
Office Communication dated Sep. 27, 2012 for Great Britain Application No. GB1208610.4.
Belfield et al., New highly efficient two-photon fluorescent dyes. Proc SPIE. 2004;5351:173-80.

(Continued)

*Primary Examiner* — Matthew Coughlin
(74) *Attorney, Agent, or Firm* — Wolf, Greenfield & Sacks, P.C.

(57) ABSTRACT

A polymer comprising one or more optionally substituted repeat units of formula (I): (I) wherein each $Ar^1$ independently represents a substituted or unsubstituted aromatic or heteroaromatic group; each $Ar^2$ independently represents a substituted or unsubstituted aromatic or heteroaromatic group; n and m in each occurrence is at least 1; and $R^1$ and $R^2$ are substituents wherein $R^1$ and $R^2$ are different.

(I)

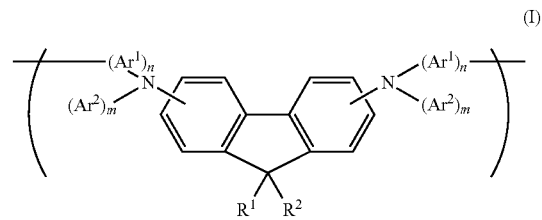

17 Claims, 4 Drawing Sheets

(51) Int. Cl.
*H01L 51/50* (2006.01)
*H01L 51/52* (2006.01)

(56) References Cited

U.S. PATENT DOCUMENTS

| | | | | |
|---|---|---|---|---|
| 9,269,905 | B2 * | 2/2016 | Tanaka | B82Y 10/00 |
| 9,331,284 | B2 * | 5/2016 | Fukushima | H01L 51/0043 |
| 9,548,467 | B2 * | 1/2017 | Archer | H01L 51/5028 |
| 9,559,307 | B2 * | 1/2017 | Steudel | H01L 51/0043 |
| 2004/0262574 | A1 | 12/2004 | Suzuki et al. | |
| 2009/0261711 | A1 | 10/2009 | Ito et al. | |
| 2011/0127516 | A1 * | 6/2011 | Nakatani | C07C 25/22 257/40 |

FOREIGN PATENT DOCUMENTS

| | | | |
|---|---|---|---|
| EP | 2 112 184 A1 | 10/2009 | |
| EP | 2 112 185 | 10/2009 | |
| EP | 2 159 245 A1 | 3/2010 | |
| GB | 2 447 173 A | 9/2008 | |
| JP | 11-185965 | 7/1999 | |
| JP | 2001-166519 | 6/2001 | |
| JP | 2001-226331 | 8/2001 | |
| JP | 2002-040686 | 2/2002 | |
| JP | 2004-212959 | 7/2004 | |
| JP | 2005 062301 | 3/2005 | |
| JP | 2005 169781 | 6/2005 | |
| JP | 2005 208110 | 8/2005 | |
| JP | 2009 016739 | 1/2009 | |
| JP | 2010-037312 | 2/2010 | |
| WO | WO 02/051958 A1 | 7/2002 | |
| WO | WO 2005/104263 A1 | 11/2005 | |
| WO | WO 2008/120470 A1 | 10/2008 | |
| WO | WO 2008120470 A1 * | 10/2008 | C08G 61/126 |
| WO | WO 2010013723 A1 * | 2/2010 | C07C 25/22 |

OTHER PUBLICATIONS

Hreha et al., Synthesis of acrylate and norbornene polymers with pendant 2,7-bis(diarylamino)fluorene hole-transport groups. Tetrahedron. 2004;60(34):7169-76.

* cited by examiner

POLYMER COMPRISING AN UNSYMMETRIC DIARYLAMINOFLUORENE UNIT

RELATED APPLICATIONS

The present application is a national stage filing under 35 U.S.C. § 371 of international PCT application, PCT/GB2013/050088, filed Jan. 16, 2013, which claims priority to United Kingdom patent application, GB 1200619.3, filed Jan. 16, 2012, and United Kingdom patent application, GB 1208610.4, filed May 16, 2012.

FIELD OF THE INVENTION

The present invention relates to polymers, in particular charge transporting and/or light-emitting polymers; monomers for making said polymers; methods of making said polymers; compositions containing said polymers; organic electronic devices comprising said polymers; and methods of making said devices.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Suitable light-emitting materials include small molecule, polymeric and dendrimeric materials. Exemplary light-emitting polymers include poly(arylene vinylenes) such as poly (p-phenylene vinylenes) and polyarylenes such as polyfluorenes.

WO 2005/049546 discloses polymers having a repeat unit of formula:

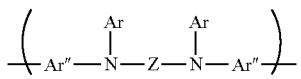

wherein Ar is a substituted or unsubstituted aryl group, Ar″ is a substituted or unsubstituted arylene group and Z is a polycyclic arylene. In one example, Z is fluorene.

US 2011/0175072 discloses an OLED including an emitting layer doped with an iridium complex and with a compound of formula:

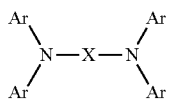

wherein Ar is aryl and X is an arylene group, for example phenylene, biphenylene and spirofluorenylene.

KR 2011/057078 discloses a compound having the following formula:

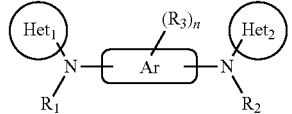

wherein Ar is biphenyl, fluorenyl or tetrahydropyrenyl, $R_1$, $R_2$ and $R_3$ are H or certain substituents, $Het_1$ and $Het_2$ are substituted or unsubstituted C3-20 heteroaryl, and n is 0-20.

US 2004/109955 discloses repeat units having the following formula:

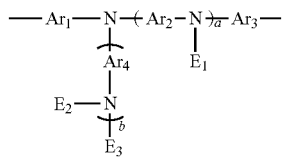

Wherein Ar1, Ar2, Ar3 and Ar4 each independently represent an arylene group or divalent heterocyclic group; E1, E2 and E3 each independently represent an aryl group which has three or more substituents selected from certain substituents or a heterocyclic group which has one or more substituents selected from certain substituents, a and be each independently represent 0 or 1 and 0≤a+b≤1.

SUMMARY OF THE INVENTION

In a first aspect, the invention provides a polymer comprising one or more repeat units of formula (I):

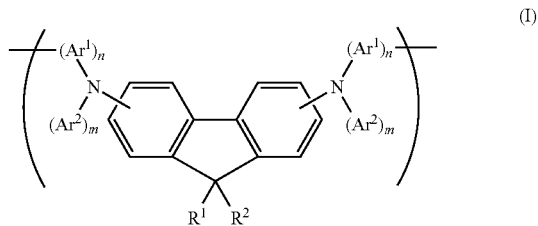

wherein each $Ar^1$ independently represents a substituted or unsubstituted aromatic or heteroaromatic group; each $Ar^2$ independently represents a substituted or unsubstituted aromatic or heteroaromatic group; n and m in each occurrence are independently at least 1; and $R^1$ and $R^2$ are substituents wherein $R^1$ and $R^2$ are different.

Optionally, $R^1$ is bound to the fluorene ring through an $sp^2$-hybridised carbon atom and $R^2$ is bound to the fluorene unit through an $sp^3$-hybridised carbon atom.

Optionally, $R^2$ is a substituted or unsubstituted branched, linear or cyclic alkyl group, optionally a $C_{1-20}$ alkyl group, wherein one or more non-adjacent C atoms may be replaced with O, S, $NR^5$, C=O or —COO— and one or more H atoms may be replaced with F or D, and $R^5$ is H or a substituent.

Optionally, $R^1$ is bound to the fluorene unit through a group —$(Ar^3)_y$, wherein $Ar^3$ in each occurrence is a substituted or unsubstituted aromatic or heteroaromatic group; y is at least 1, optionally 1, 2 or 3; and —(Ar³)$_y$ forms a linear or branched chain of Ar³ groups when y is greater than 2.

Optionally, Ar³, or at least one Ar³ in the case where y is greater than 1, is a substituted or unsubstituted aromatic or heteroaromatic group.

Optionally, Ar³ in each occurrence is a substituted or unsubstituted phenyl.

Optionally, Ar³ is substituted with one or more substituents, optionally one or more substituents selected from F; CN; NO$_2$; NR$^5_2$; a crosslinkable group; and C$_{1-20}$ alkyl wherein one or more non-adjacent C atoms may be replaced with optionally substituted aryl or heteroaryl, O, S, NR$^5$, C=O or —COO— and wherein one or more H atoms may be replaced with F or D, and R$^5$ is H or a substituent.

Optionally, each n is independently 1-3, preferably 1.

Optionally, each m independently 1-3, preferably 1.

Optionally, each Ar¹ and Ar² is independently an unsubstituted or substituted phenyl.

Optionally, each Ar¹ is unsubstituted.

Optionally, at least one Ar² is substituted with one or more substituents selected from F; CN; NO$_2$; NR$^5_2$; a crosslinkable group; C$_{1-20}$ alkyl groups wherein one or more non-adjacent C atoms may be replaced with optionally substituted aryl or heteroaryl, O, S, NR$^5$, C=O or —COO— and wherein one or more H atoms may be replaced with F or D, and R$^5$ is H or a substituent.

Optionally, m is 1 and at least one Ar² is substituted with at least two substituents, optionally 2 or 3 substituents.

Optionally, at least one position of at least one (Ar²)$_m$ that is ortho- to the Ar²—N bond is substituted.

Optionally, the polymer comprises at least one co-repeat unit.

Optionally, the polymer comprises a co-repeat unit of formula (IV):

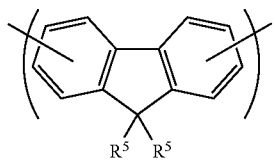

wherein R$^5$ in each occurrence is the same or different and is H or a substituent, and wherein the two groups R$^5$ may be linked to form a ring.

Optionally, the polymer comprises a repeat unit of formula (Ib):

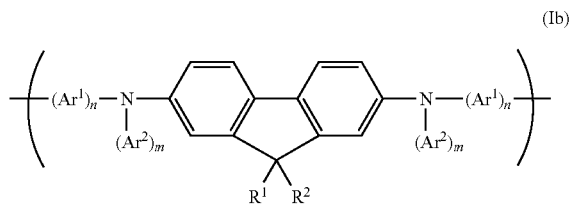

wherein Ar¹, Ar², R¹, R², n and m are as described above.

Optionally, the polymer is crosslinkable.

Optionally, the repeat unit of formula (I) and/or one or more co-repeat units are substituted with at least one crosslinkable group.

Optionally, the at least one crosslinkable group is independently in each occurrence selected from a double bond group and a benzocyclobutane group.

In a second aspect, the invention provides an organic electronic device comprising a semiconductor layer wherein the semiconductor layer comprises a polymer according to the first aspect.

Optionally according to the second aspect, the device is an organic light-emitting device comprising the semiconductor layer between an anode and a cathode.

Optionally according to the second aspect, the semiconductor layer is a light-emitting layer.

Optionally according to the second aspect, the semiconducting layer is a hole-transporting layer between the anode and a light-emitting layer.

In a third aspect the invention provides a formulation comprising a polymer according to the first aspect and at least one solvent.

In a fourth aspect the invention provides a method of forming an organic electronic device according to the second aspect, the method comprising the step of forming the semiconducting layer by depositing the formulation of the third aspect and evaporating the at least one solvent.

In a fifth aspect, the invention provides a monomer of formula (II):

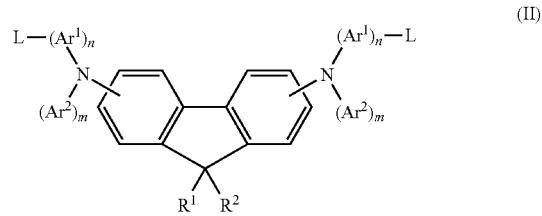

wherein Ar¹, Ar², R¹, R², n and m are as described in the first aspect, and each L represents a reactive leaving group.

Optionally according to the fifth aspect, each L is a group capable of participating in a metal-mediated cross-coupling reaction.

Optionally according to the fifth aspect, each L is independently selected from the group consisting of halogen, preferably Br or I; boronic acids and esters thereof; and sulfonic acid esters.

In a sixth aspect the invention provides a method of forming a polymer according to the first aspect comprising the step of polymerising a monomer according to the fifth aspect.

Optionally according to the sixth aspect the polymerisation is carried out in the presence of a metal catalyst.

Optionally according to the sixth aspect the metal catalyst is selected from nickel and palladium catalysts.

In a seventh aspect the invention provides a polymer comprising repeat units of formula (III):

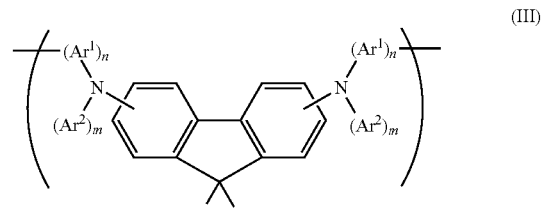

wherein each $Ar^1$ independently represents a substituted or unsubstituted aromatic or heteroaromatic group; each $Ar^2$ independently represents a substituted or unsubstituted aromatic or heteroaromatic group; n and m in each occurrence are independently at least 1; and $R^3$ and $R^4$ are substituents wherein at least one of $R^3$ and $R^4$ is a substituted or unsubstituted aryl or heteroaryl group.

Optionally according to the seventh aspect $R^3$ and $R^4$ both represent a substituted or unsubstituted aryl or heteroaryl group.

Optionally according to the seventh aspect at least one of $R^3$ and $R^4$ has formula $(Ar^6)_z$ wherein $Ar^6$ in each occurrence represents an unsubstituted or substituted aromatic or heteroaromatic group and z is at least 1, optionally 1, 2 or 3.

Optionally according to the seventh aspect $Ar^6$ is unsubstituted or substituted phenyl.

Optionally according to the seventh aspect at least one $Ar^6$ is substituted with one or more substituents selected from F; CN; $NO_2$; $NR^5_2$; a crosslinkable group; and $C_{1-20}$ alkyl wherein one or more non-adjacent C atoms may be replaced with optionally substituted aryl or heteroaryl, O, S, $NR^5$, C=O or —COO— and wherein one or more H atoms may be replaced with F or D, and $R^5$ is H or a substituent.

It will be understood that polymers comprising repeat units of formula (III) may be structured, made and used as described in any part of the first to sixth aspects of the invention, and that $Ar^1$, $Ar^2$, m and n of repeat units of formula (III) may be as described with respect to repeat units of formula (I).

"aromatic group" and "heteroaromatic group" includes monocyclic or polycyclic aromatic and heteroaromatic groups, respectively.

DESCRIPTION OF THE DRAWINGS

The invention will now be described in more detail with reference to the drawings in which.

DETAILED DESCRIPTION OF THE INVENTION

Figure 1:
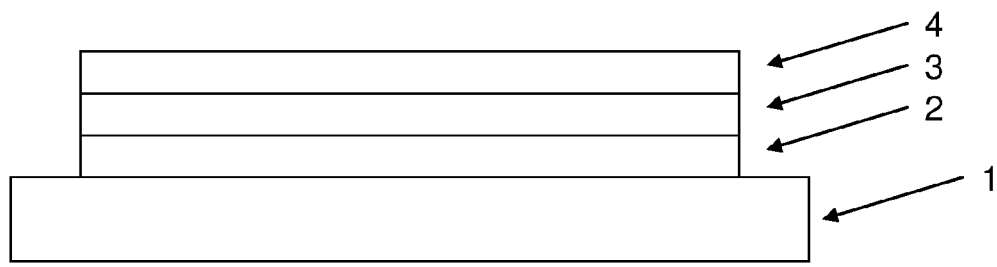
FIG. 1 illustrates schematically an OLED according to an embodiment of the invention.

FIG. 1, which is not drawn to any scale, illustrates schematically an OLED according to an embodiment of the invention. The OLED is carried on substrate 1 and comprises an anode 2, a cathode 4 and a light-emitting layer 3 between the anode and the cathode. Further layers (not shown) may be provided between the anode and the cathode including, without limitation, charge-transporting layers, charge-blocking layers and charge injection layers. The device may contain more than one light-emitting layer.

Exemplary OLED structures including one or more further layers include the following:
Anode/Hole-injection layer/Light-emitting layer/Cathode
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

The polymer of the invention may be provided in a light-emitting layer and/or in one or more charge-transporting layers. In one preferred embodiment, a polymer of the invention is provided in at least a hole-transporting layer. In a preferred embodiment, a polymer of the invention is provided in at least a light-emitting layer. If used in a light-emitting layer, a polymer of the invention may be a blue light-emitting material or may be a host for a fluorescent or phosphorescent dopant.

One or more of the sp2-hybridised carbon atoms of the central fluorene of the repeat unit of formula (I) that is not substituted with $N(Ar^1)_n(Ar^2)_m$ may be unsubstituted or substituted with one or more substituents. Suitable substituents include F, CN, $NO_2$ and $C_{1-20}$ alkyl, wherein one or more non-adjacent C atoms may be replaced with O, S, NH or substituted N, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups. Where substituents are present, they are preferably provided on at least one of the 4- and 5-positions of the fluorene ring.

Exemplary repeat units of formula (I) include the following:

wherein Alk in each occurrence independently represents $C_{1-20}$ alkyl and b in each occurrence is independently 0 or an integer, optionally 0, 1, 2 or 3.

The polymer may be a homopolymer, or may be a copolymer comprising a repeat unit of formula (I) and one or more further co-repeat units. In the case of a copolymer, the molar percentage of repeat units of formula (I) may be in the range of 1-99 mol %. The molar percentage of repeat units of formula (I) may depend on the application of the device. For example, repeat units of formula (I) may be provided in an amount in the range of 20 mol %-60 mol %, optionally 30-60 mol % of the total number of repeat units of a polymer for use in a hole-transporting layer, or may be in the range of about 1 mol %-50 mol %, optionally 1 mol %-30 mol %, of the total number of repeat units of a polymer for use in a light-emitting layer.

The polymer may contain only one repeating unit of formula (I), or may contain two or more different repeat units of formula (I).

The polymer may have a HOMO level in the range of 4.8-5.5 eV, optionally 5.1-5.3 eV.

HOMO and LUMO levels may be measured by square wave cyclic voltammetry. Apparatus to measure HOMO or LUMO energy levels by CV may comprise a cell containing a tert-butyl ammonium perchlorate/or tertbutyl ammonium hexafluorophosphate solution in acetonitrile, a glassy carbon working electrode where the sample is coated as a film, a platinum counter electrode (donor or acceptor of electrons) and a reference glass electrode no leak Ag/AgCl. Ferrocene is added in the cell at the end of the experiment for calculation purposes. (Measurement of the difference of potential between Ag/AgCl/ferrocene and sample/ferrocene).

Method and Settings:

3 mm diameter glassy carbon working electrode

Ag/AgCl/no leak reference electrode

Pt wire auxiliary electrode 0.1 M tetrabutylammonium hexafluorophosphate in acetonitrile LUMO=4.8−ferrocene (peak to peak maximum average)+onset Sample: 1 drop of 5 mg/mL in toluene spun @3000 rpm LUMO (reduction) measurement:

A good reversible reduction event is typically observed for thick films measured at 200 mV/s and a switching potential of −2.5V. The reduction events should be measured and compared over 10 cycles, usually measurements are taken on the 3$^{rd}$ cycle. The onset is taken at the intersection of lines of best fit at the steepest part of the reduction event and the baseline.

When cyclic voltammetry reaches a set potential the working electrode's potential ramp is inverted. This inversion can happen multiple times during a single experiment. The current at the working electrode is plotted versus the applied voltage to give the cyclic voltammogram trace.

The polymer may comprise crosslinkable groups for crosslinking the polymer. Crosslinkable groups may be provided as substituents of repeat units formula (I), and/or may be provided in a separate co-repeat unit. Exemplary crosslinkable groups include groups comprising a reactive double bond and groups comprising benzocyclobutane. Reactive double bond groups include groups with a terminal =CH$_2$ unit. The crosslinkable group may be bound directly to a repeat unit or end group of the polymer or spaced apart therefrom by a spacer group, for example a C$_{1-10}$ alkyl spacer group.

The crosslinkable group may have formula (VI):

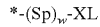

(VI)

wherein Sp represents a spacer group, for example C$_{1-10}$ alkyl; w is 0 or 1; XL represents a crosslinkable group; and * represents a point of attachment of the crosslinkable group to the polymer.

Exemplary crosslinkable groups include the following:

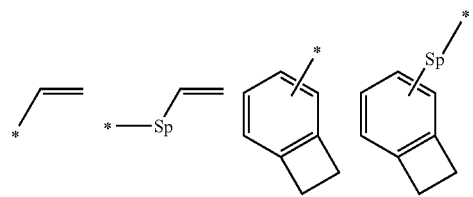

each of which may be unsubstituted or substituted with one or more substituents, for example one or more C$_{1-10}$ alkyl groups.

In use, a polymer comprising crosslinkable groups may be deposited to form a layer of the device and the crosslinkable groups may be crosslinked in order to form a crosslinked layer that is substantially resistant to dissolution upon exposure of the crosslinked layer to a solvent (for example, upon deposition of a further layer of the device on the crosslinked layer by a solution processing method). Crosslinkable groups may be used if the polymer is to form the hole-transporting layer of an OLED with an overlying light-emitting layer.

The repeat units of formula (I) may be conjugated to one or more co-repeat units, and the polymer may be a conjugated copolymer. Exemplary co-repeat units of a conjugated copolymer include optionally substituted monocyclic and polycyclic arylene repeat units as disclosed in for example, Adv. Mater. 2000 12(23) 1737-1750 and include: 1,2-, 1,3- and 1,4-phenylene repeat units as disclosed in J. Appl. Phys. 1996, 79, 934; 2,7-fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as C$_{1-20}$ alkyl or alkoxy; electron withdrawing groups such as fluorine, nitro or cyano; and substituents for increasing glass transition temperature (Tg) of the polymer.

One exemplary class of arylene repeat units is optionally substituted fluorene repeat units, such as repeat units of formula (IV):

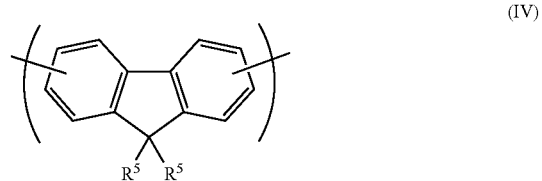

(IV)

wherein R$^5$ in each occurrence is the same or different and is H or a substituent, and wherein the two groups R$^5$ may be linked to form a ring.

Each R$^5$ is preferably a substituent, and each R$^5$ may independently be selected from the group consisting of:

substituted or unsubstituted alkyl, optionally C$_{1-20}$ alkyl, wherein one or more non-adjacent C atoms may be replaced with optionally substituted aryl or heteroaryl, O, S, substituted N, C=O or —COO— and one or more H atoms may be replaced with F;

substituted or unsubstituted aryl or heteroaryl group, or a linear or branched chain of aryl or heteroaryl, each of which may independently be substituted, for example a group of formula —(Ar$^4$)$_r$ wherein Ar$^4$ in each occurrence independently is a substituted or unsubstituted aryl or heteroaryl and r is at least 1, optionally 1, 2 or 3;

a crosslinkable group attached directly to the fluorene unit or spaced apart therefrom by a spacer group, for example a group comprising a double bond such and a vinyl or acrylate group, or a benzocyclobutane group, for example a crosslinkable group of formula (VI) as described above.

In the case where $R^5$ comprises one or more aryl or heteroaryl group $Ar^4$, each $Ar^4$ may independently be substituted with one or more substituents $R^6$ selected from the group consisting of:

alkyl, for example $C_{1-20}$ alkyl, wherein one or more non-adjacent C atoms may be replaced with O, S, substituted N, C=O and —COO— and one or more H atoms of the alkyl group may be replaced with F or aryl or heteroaryl optionally substituted with one or more groups $R^7$, aryl or heteroaryl optionally substituted with one or more groups $R^7$, $NR^8_2$, $OR^8$, $SR^8$, and fluorine, nitro and cyano;

wherein each $R^7$ is independently alkyl, for example $C_{1-20}$ alkyl, in which one or more non-adjacent C atoms may be replaced with O, S, substituted N, C=O and —COO— and one or more H atoms of the alkyl group may be replaced with F or D; and each $R^8$ is independently selected from the group consisting of alkyl, for example $C_{1-20}$ alkyl, and aryl or heteroaryl optionally substituted with one or more alkyl groups, for example phenyl that is unsubstituted or substituted with one or more $C_{1-20}$ alkyl groups.

Substituents $R^5$ as described herein with reference to formula (IV) are also applicable to groups $NR^5$, or $NR^5_2$ of repeat units of formula (I) as described with respect to the first aspect of the invention.

Optional substituents for the fluorene unit, other than substituents $R^5$, are preferably selected from the group consisting of alkyl, for example $C_{1-20}$ alkyl, wherein one or more non-adjacent C atoms may be replaced with O, S, NH or substituted N, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

Where present, substituted N may independently in each occurrence be $NR^9$ wherein $R^9$ is alkyl, optionally $C_{1-20}$ alkyl, or optionally substituted aryl or heteroaryl. Optional substituents for aryl or heteroaryl $R^9$ may be selected from $R^7$ or $R^8$.

Preferably, each $R^5$ is selected from the group consisting of $C_{1-20}$ alkyl and —$(Ar^4)_r$ wherein $Ar^4$ in each occurrence is substituted or unsubstituted substituted phenyl. Optional substituents for phenyl include one or more $C_{1-20}$ alkyl groups.

The repeat unit of formula (IV) may be a 2,7-linked repeat unit of formula (IVa):

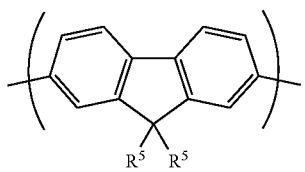

Optionally, the repeat unit of formula (IVa) is not substituted in a position adjacent to the 2- or 7-positions.

The extent of conjugation of repeat units of formula (IV) to adjacent repeat units may be limited by (a) linking the repeat unit through the 3- and/or 6-positions to limit the extent of conjugation across the repeat unit, and/or (b) substituting the repeat unit with one or more further substituents $R^5$ in or more positions adjacent to the linking positions in order to create a twist with the adjacent repeat unit or units, for example a 2,7-linked fluorene carrying a $C_{1-20}$ alkyl substituent in one or both of the 3- and 6-positions. Inclusion of twisting units in the polymer may be advantageous for use of the polymer in a device containing one or more phosphorescent light-emitting materials to avoid quenching of phosphorescence.

Another exemplary class of arylene repeat units is phenylene repeat units, such as phenylene repeat units of formula (V):

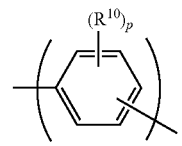

wherein p is 0, 1, 2, 3 or 4, optionally 1 or 2, and $R^{10}$ independently in each occurrence is a substituent, optionally a substituent $R^5$ as described above, for example $C_{1-20}$ alkyl, and phenyl that is unsubstituted or substituted with one or more $C_{1-20}$ alkyl groups.

The repeat unit of formula (V) may be 1,4-linked, 1,2-linked or 1,3-linked.

If the repeat unit of formula (V) is 1,4-linked and if p is 0 then the extent of conjugation of repeat unit of formula (V) to one or both adjacent repeat units may be relatively high.

If p is at least 1, and/or the repeat unit is 1,2- or 1,3 linked, then the extent of conjugation of repeat unit of formula (V) to one or both adjacent repeat units may be relatively low. In one optional arrangement, the repeat unit of formula (V) is 1,3-linked and p is 0, 1, 2 or 3. In another optional arrangement, the repeat unit of formula (V) has formula (Va):

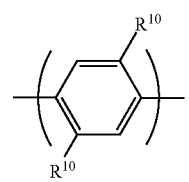

Another exemplary arylene repeat unit has formula (VII):

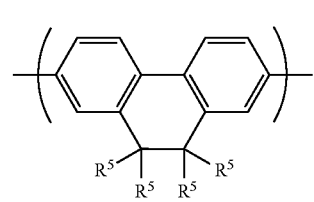

wherein $R^5$ is as described with reference to formula (IV) above. Each of the $R^5$ groups may be linked to any other of the $R^5$ groups to form a ring.

Further arylene co-repeat units include: phenanthrene repeat units; naphthalene repeat units; anthracene repeat units; and perylene repeat units. Each of these arylene repeat units may be linked to adjacent repeat units through any two of the aromatic carbon atoms of these units. Specific exemplary linkages include 9,10-anthracene; 2,6-anthracene; 1,4-naphthalene; 2,6-naphthalene; 2,7-phenanthrene; and 2,5-perylene.

The polymer may comprise amine repeat units of formula (VIII):

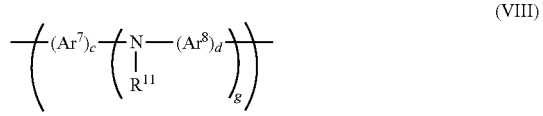

(VIII)

wherein $Ar^7$ and $Ar^8$ in each occurrence are independently selected from substituted or unsubstituted aryl or heteroaryl, g is greater than or equal to 1, preferably 1 or 2, $R^{11}$ is H or a substituent, preferably a substituent, and c and d are each independently 1, 2 or 3, with the proviso that $Ar^8$ is not fluorene in the case where g is 2.

$R^{11}$, which may be the same or different in each occurrence when g>1, is preferably selected from the group consisting of alkyl, for example $C_{1-20}$ alkyl, $Ar^9$, a branched or linear chain of $Ar^9$ groups, or a crosslinkable unit that is bound directly to the N atom of formula (VIII) or spaced apart therefrom by a spacer group, wherein $Ar^9$ in each occurrence is independently optionally substituted aryl or heteroaryl. Exemplary spacer groups are $C_{1-20}$ alkyl, phenyl and phenyl-$C_{1-20}$ alkyl.

Any of $Ar^7$, $Ar^8$ and, if present, $Ar^9$ in the repeat unit of Formula (VI) may be linked by a direct bond or a divalent linking atom or group to another of $Ar^7$, $Ar^8$ and $Ar^9$. Preferred divalent linking atoms and groups include O, S; substituted N; and substituted C.

Any of $Ar^7$, $Ar^8$ and, if present, $Ar^9$ may be substituted with one or more substituents. Exemplary substituents are substituents $R^5$ as described above.

In one preferred arrangement, $R^{11}$ is $Ar^9$ and each of $Ar^7$, $Ar^8$ and $Ar^9$ are independently and optionally substituted with one or more $C_{1-20}$ alkyl groups.

$Ar^7$, $Ar^8$ and $Ar^9$ are preferably phenyl, each of which may independently be substituted with one or more substituents as described above.

In another preferred arrangement, $Ar^7$ and $Ar^8$ are phenyl, each of which may be substituted with one or more $C_{1-20}$ alkyl groups, and $R^{11}$ is 3,5-diphenylbenzene wherein each phenyl may be substituted with one or more $C_{1-20}$ alkyl groups.

In another preferred arrangement, c, d and g are each 1 and $Ar^7$ and $Ar^8$ are phenyl linked by an oxygen atom to form a phenoxazine ring.

Polymer Synthesis

Preferred methods for preparation of conjugated polymers, such as homopolymer or copolymer comprising repeat units of formula (I) as described above, comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable pi-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end-capping group or side group carrying only one reactive leaving group may be bound to the polymer by reaction of a leaving group at the polymer chain end or side respectively.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular copolymers may be prepared when both reactive groups of a first monomer are boron and both reactive groups of a second monomer are halogen.

As alternatives to halides, other leaving groups capable of participating in metal insertion include sulfonic acids and sulfonic acid esters such as tosylate, mesylate and triflate.

Light-Emitting Layers

Suitable light-emitting materials for use in the light-emitting layer or layers of an OLED include small molecule, polymeric and dendrimeric materials, and compositions thereof. Suitable light-emitting polymers include conjugated polymers, for example substituted or unsubstituted poly (arylene vinylenes) such as poly(p-phenylene vinylenes) and substituted or unsubstituted polyarylenes such as: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. Such polymers as disclosed in, for example, Adv. Mater. 2000 12(23) 1737-1750 and references therein. A polymer comprising a repeat unit of formula (I) as described above may be provided in the light emitting layer of an OLED, either as a light-emitting material or as a host for a fluorescent or phosphorescent dopant.

The light-emitting layer may consist of a light-emitting material alone, or may comprise this material in combination with one or more further materials. In particular, the light-emitting material may be blended with hole and/or electron transporting materials or alternatively may be covalently bound to hole and/or electron transporting materials as disclosed in for example, WO 99/48160.

Light-emitting copolymers may comprise a light-emitting region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality—for example, an amine unit of formula (I) as described above may provide both hole transport and light-emission functionality. A light-emitting copolymer comprising light-emitting repeat units and one or both of a hole transporting repeat units and electron transporting repeat units may provide said units in a polymer main-chain, as per U.S. Pat. No. 6,353,083, or in polymer side-groups pendant from the polymer backbone.

In the case of a fluorescent light-emitting layer, the light-emitting layer may comprise a triplet-quencher capable of accepting triplet excitons generated by the light-emitting material. The triplet quencher may have a triplet energy level lower than that of the light-emitting material to allow transfer to triplets and a singlet energy level higher than that of the light-emitting material to avoid quenching or down-conversion of fluorescence. The triplet quencher may be provided as a repeat unit of a light-emitting polymer or may be blended with a light-emitting material.

Suitable light-emitting materials may emit in the UV, visible and/or infra-red region of the electromagnetic spectrum. The OLED may contain one or more of red, green and blue light-emitting materials.

A blue light-emitting material as described anywhere herein may have photoluminescent spectrum with a peak wavelength in the range of less than or equal to 480 nm, such as in the range of 400-480 nm A green light-emitting material as described anywhere herein may have photoluminescent spectrum with a peak wavelength in the range of above 480 nm-560 nm.

A red light-emitting material as described anywhere herein may have photoluminescent spectrum with a peak wavelength in the range of above 560 nm-630 nm.

More than one light-emitting material may be used. For example, red, green and blue light-emitting dopants may be used to obtain white light emission.

The light emitting layer may comprise a host material and at least one light-emitting dopant. The host material may be a material as described above that would, in the absence of a dopant, emit light itself, and may be a polymer comprising a repeat unit of formula (I) as described above. When a host material and dopant are used in a device, the dopant alone may emit light. Alternatively, the host material and one or more dopants may emit light. White light may be generated by emission from multiple light sources, such as emission from both the host and one or more dopants or emission from multiple dopants.

In the case of a fluorescent light-emitting dopant the singlet excited state energy level ($S_1$) of the host material should be higher than that of the fluorescent light-emitting dopant in order that singlet excitons may be transferred from the host material to the fluorescent light-emitting dopant. Likewise, in the case of a phosphorescent light-emitting dopant the triplet excited state energy level ($T_1$) of the host material should be higher than that of the phosphorescent light-emitting dopant in order that triplet excitons may be transferred from the host material to the fluorescent light-emitting dopant.

Exemplary phosphorescent light-emitting dopants include metal complexes comprising substituted or unsubstituted complexes of formula (X):

$$ML^1{}_q L^2{}_r L^3{}_s \qquad (X)$$

wherein M is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium are particularly preferred.

Exemplary ligands $L^1$, $L^2$ and $L^3$ include carbon or nitrogen donors such as porphyrin or bidentate ligands of formula (XI):

wherein $Ar^4$ and $Ar^5$ may be the same or different and are independently selected from substituted or unsubstituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

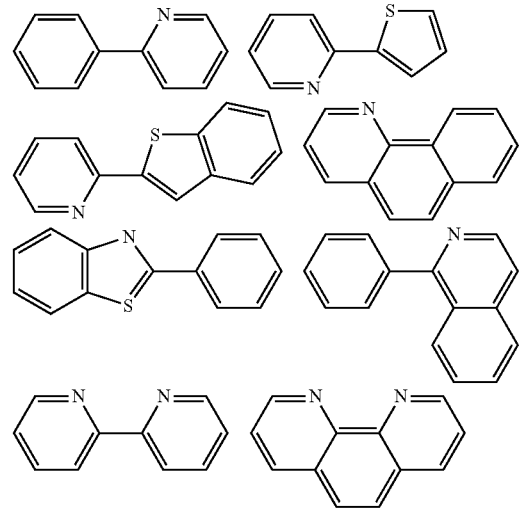

Each of $Ar^4$ and $Ar^5$ may carry one or more substituents. Two or more of these substituents may be linked to form a ring, for example an aromatic ring.

Other ligands suitable for use with d-block elements include diketonates, in particular acetylacetonate (acac); triarylphosphines and pyridine, each of which may be substituted.

Exemplary substituents include groups $R^5$ as described above with reference to Formula (IV). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; bromine, chlorine or iodine which can serve to functionalise the ligand for attachment of further groups, for example as disclosed in WO 02/68435 and EP 1245659; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (XII)

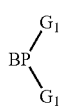

(XII)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIIa):

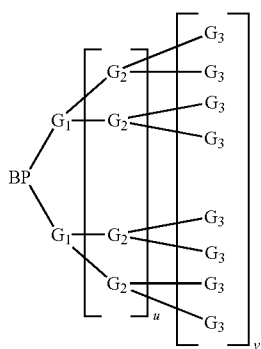

(XIIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups.

BP and/or any group G may be substituted with one or more substituents, for example one or more $C_{1-20}$ alkyl or alkoxy groups.

Where used, a light-emitting dopant may be present in an amount of about 0.05 mol % up to about 20 mol %, optionally about 0.1-10 mol % relative to their host material.

The light-emitting dopant may be physically mixed with the host material or it may be chemically bound to the host material in the same manner described above with respect to binding of the light-emitting dopant to the charge transporting material.

More than one light-emitting layer may be present. Multiple light-emitting layers may together produce white light.

The light-emitting layer may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

Charge Transporting and Charge Blocking Layers

A hole transporting layer may be provided between the anode and the light-emitting layer or layers. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

A charge-transporting layer or charge-blocking layer may be crosslinked, particularly if a layer overlying that charge-transporting or charge-blocking layer is deposited from a solution. The crosslinkable group used for this crosslinking may be a crosslinkable group comprising a reactive double bond such and a vinyl or acrylate group, or a benzocyclobutane group.

If present, a hole transporting layer located between the anode and the light-emitting layers preferably has a HOMO level of less than or equal to 5.5 eV, more preferably around 4.8-5.5 eV or 5.1-5.3 eV as measured by cyclic voltammetry. The HOMO level of the hole transport layer may be selected so as to be within 0.2 eV, optionally within 0.1 eV, of an adjacent layer (such as a light-emitting layer) in order to provide a small barrier to hole transport between these layers.

If present, an electron transporting layer located between the light-emitting layers and cathode preferably has a LUMO level of around 3-3.5 eV as measured by cyclic voltammetry. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

A hole transporting layer may contain a homopolymer or copolymer comprising a repeat unit of formula (I) as described above An electron transporting layer may contain a polymer comprising a chain of optionally substituted arylene repeat units, such as a chain of fluorene repeat units.

Hole Injection Layers

A conductive hole injection layer, which may be formed from a conductive organic or inorganic material, may be provided between the anode 2 and the light-emitting layer 3 illustrated in FIG. 1 to assist hole injection from the anode into the layer or layers of semiconducting polymer. Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Cathode

The cathode is selected from materials that have a workfunction allowing injection of electrons into the light-emitting layer. Other factors influence the selection of the cathode such as the possibility of adverse interactions between the cathode and the light-emitting material. The cathode may consist of a single material such as a layer of aluminium. Alternatively, it may comprise a plurality of metals, for example a bilayer of a low workfunction material and a high workfunction material such as calcium and aluminium as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to preventingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Suitable solvents for forming compositions of the polymer for solution processing include common organic solvents, including mono- or poly-alkylbenzenes such as toluene and xylene.

Particularly preferred solution deposition techniques including printing and coating techniques such spin-coating and inkjet printing.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Monomer Example 1

Monomer Example 1 was prepared according to the following scheme:

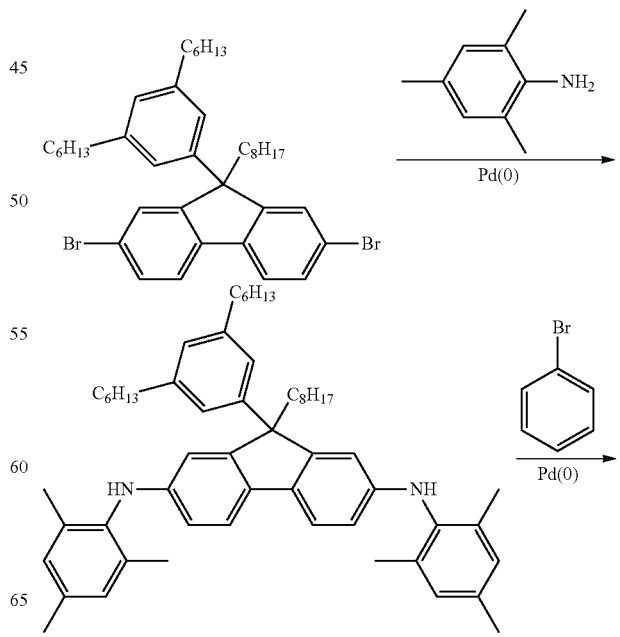

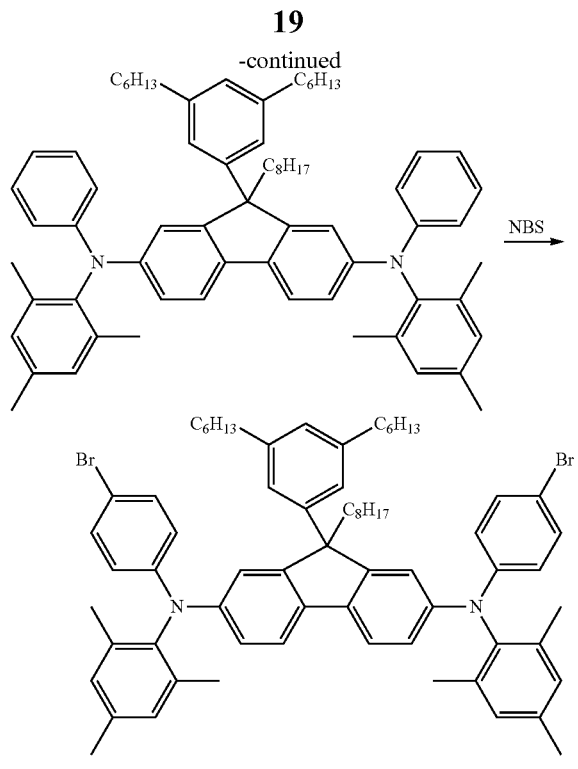

Monomer Example 1

STAGE 1: 2,7-dibromo-9-(3,5-dihexyl-phenyl)-9-octyl-fluorene (125 g, 184 mmol) and trimethyl aniline (54.63 g, 404 mmol) were charged to a 3 L flask, equipped with a mechanical stirrer, a condenser and nitrogen inlet. The mixture was sparged with nitrogen for 90 minutes. Tris (dibenzylideneacetone)dipalladium(0) (0.841 g, 0.92 mmol) and tri-tert-butyl-phosphonium tetrafluoroboronate (0.400 g, 1.38 mmol) were added and the mixture was sparged for a further 10 minutes. Sodium tert-butoxide (53 g, 552 mmol) was added portion-wise. The reaction mixture was heated to reflux for 16 hours. After cooling to room temperature, the mixture was quenched with water (400 ml). The aqueous phase was further extracted with toluene and the combined organic phases were reduced to dryness to give a dark brown oil. This was dissolved in toluene (500 ml) passed through a Celite® plug (eluting with ~1.5 L toluene and then directly filtered the eluant through a Silica plug (both Ø125 mm, height 6 cm), rinsing through with toluene. The toluene eluant was reduced to dryness by rotary evaporation. The solid was heated with IPA and dichloromethane (at 60 degrees) and upon removal of the dichloromethane and cooling, the target molecule formed a light yellow precipitate. After recrystallisation from isopropanol and toluene (9:1) a purity of 99.8% HPLC was obtained (94 g, 65% yield) after drying in a vacuum oven at 50° C.

STAGE 2: The stage 1 material (94 g, 120 mmol), bromobenzene (32 ml, 300 mmol) and toluene (1400 ml) were charged to a 3 L flask, equipped with a mechanical stirrer, a condenser and nitrogen inlet. The mixture was sparged with nitrogen for 70 minutes, then Tris(dibenzylideneacetone)dipalladium(0) (1.09 g, 1.2 mmol) and tri-tert-butyl-phosphonium tetrafluoroboronate (0.69 g, 2.4 mmol) were added and the mixture was degassed for a further 10 minutes. Sodium tert-butoxide (34.4 g, 360 mmol) was added portion-wise and the mixture degassed for 10 minutes before heating the mixture to reflux for 16 hours. Once cooled to room temperature, water was added (300 ml). The aqueous phase was separated and the organic layer was washed with more water (2×200 ml). The organic phase was reduced to dryness by rotary evaporation to give a brown oil. The oil was dissolved in the minimum amount of toluene (~200 ml) by heating at 60° C. It was passed through a plug of Celite® on Silica, eluting with toluene (Ø 100 mm; Height: 10 cm Silica with 3 cm of Celite® on top). The eluant was reduced to dryness to yield an orange oil. The oil was washed with methanol at 65° C. and the methanol was decanted. After thorough drying, the product was used directly in the next stage (82 g, HPLC 99.60% purity, 73% yield).

STAGE 3: The Stage 2 material (55.8 g, 59.3 mmol) was dissolved in chloroform (550 ml) and sparged with nitrogen. The mixture was cooled to −15° C. (internal temperature) using IPA/CO$_2$(s) bath. NBS (21.099 g, 119 mmol) in a solution of dimethyl formamide (550 ml) was added, dropwise, to the cooled solution. Once the addition was complete, the mixture was stirred at this temperature for 3 hours and then left to warm to room temperature overnight. A sample was taken for an in-process check by LCMS. Further NBS was added at −15° C. to adjust for amount of mono-bromide present (0.084 g in 5 ml DMF). The reaction was maintained at this temperature for 3 hours and then quenched by the addition of methanol (400 ml). Water (400 ml) was added to the mixture and then the chloroform was removed by rotary evaporation. A solid precipitated at this stage and this was filtered, dissolved in dichloromethane (500 ml) and washed with water, 10% sodium carbonate solution, and again with water. After extraction of the aqueous phases with dichloromethane, the combined organics were reduced to dryness. The solid was dissolved in dichloromethane (50 ml) and passed through a plug of Celite® and silica, eluting with hexane (1 L) then 20% mixture of dichloromethane: petroleum ether (80:100) until the product was fully eluted. The eluant was reduced to dryness to give a clear oil (99% purity). Further recrystallisation with isopropanol: toluene and methanol: n-butyl acetate were used to improve the purity to 99.62% HPLC, 58.8 g (62.25% yield).

Monomer Example 2

Monomer Example 2, illustrated below, was prepared using the same method described for Monomer Example 1.

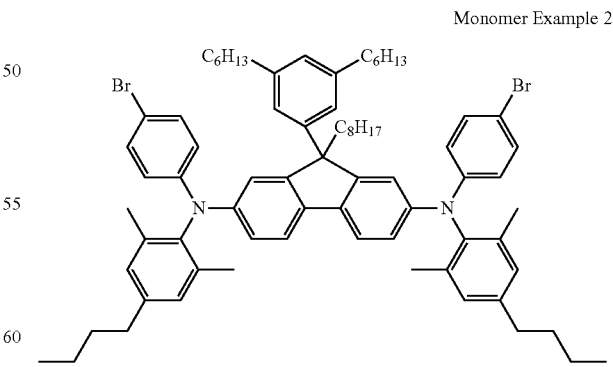

Monomer Example 2

Monomer Example 3

Monomer Example 3, illustrated below, was prepared using the same method described for Monomer Example 1.

Monomer Example 3

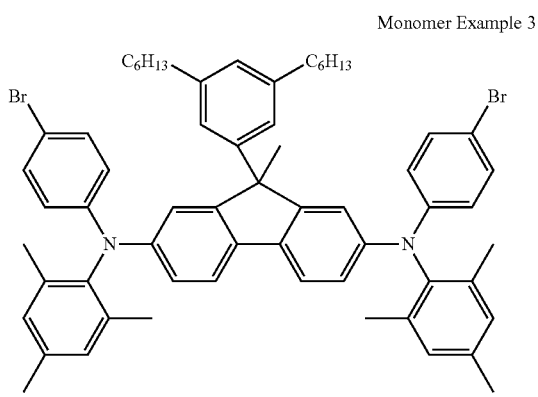

Polymer Example 1

Polymer Example 1 was prepared by Suzuki polymerisation as described in WO 00/53656 of the following monomers:

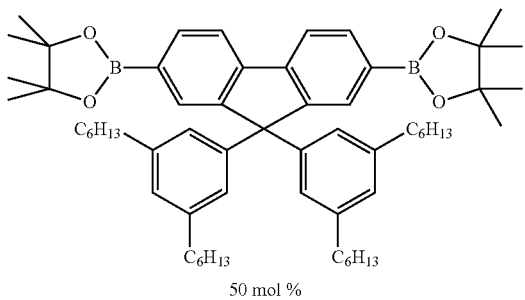

50 mol %

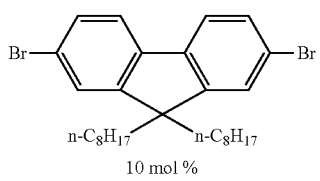

10 mol %

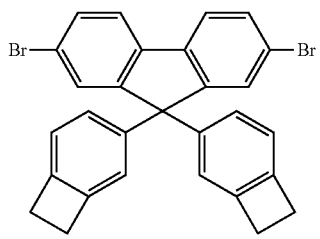

5 mol %

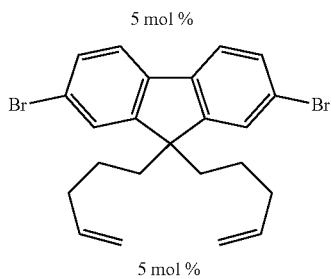

5 mol %

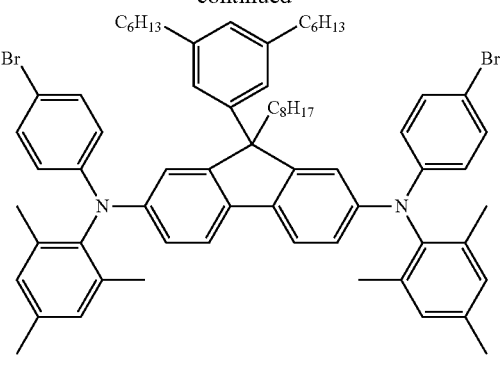

30 mol %, Monomer 1

Polymer Example 1 had a weight average molecular weight (Mw) of 370,000 and a number average molecular weight (Mn) of 96,000.

Comparative Polymer 1

Comparative Polymer 1 was prepared as described with respect to Polymer Example 1 except that Monomer Example 1 was replaced with Comparative Monomer 1 illustrated below:

Comparative Monomer 1

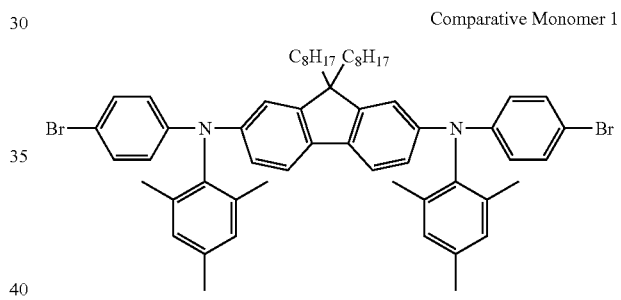

Comparative Polymer 1 had a weight average molecular weight (Mw) of 187,000 and a number average molecular weight (Mn) of 57,000.

Polymer Example 2

Polymer Example 2 was prepared by Suzuki polymerisation as described in WO 00/53656 of the following monomers:

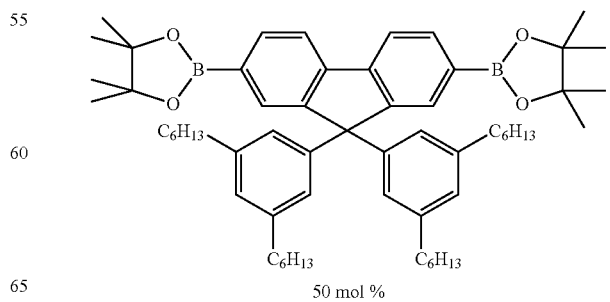

50 mol %

-continued

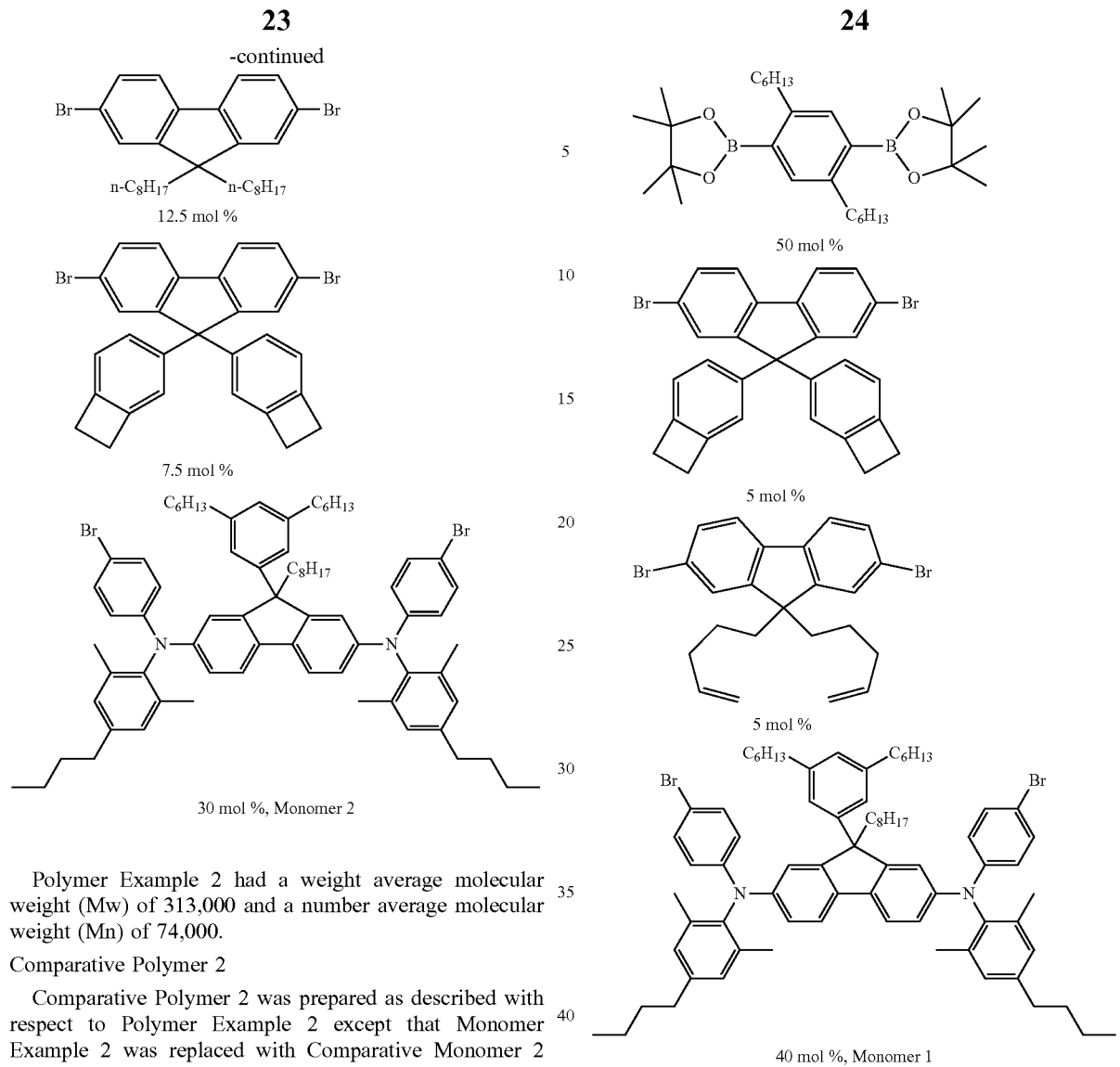

30 mol %, Monomer 2

Polymer Example 2 had a weight average molecular weight (Mw) of 313,000 and a number average molecular weight (Mn) of 74,000.

Comparative Polymer 2

Comparative Polymer 2 was prepared as described with respect to Polymer Example 2 except that Monomer Example 2 was replaced with Comparative Monomer 2 illustrated below:

Comparative Monomer 2

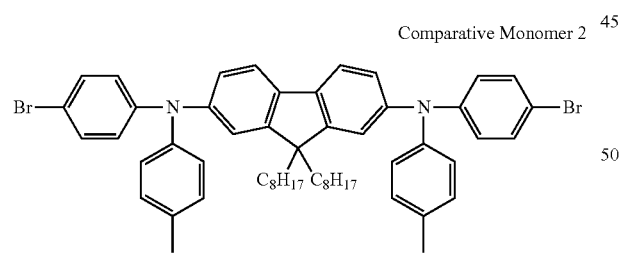

Comparative Polymer 2 had a weight average molecular weight (Mw) of 240,000 and a number average molecular weight (Mn) of 66,000.

Polymer Example 3

Polymer Example 3 was prepared by Suzuki polymerisation as described in WO 00/53656 of the following monomers:

40 mol %, Monomer 1

The polymer had a weight average molecular weight Mw of 210,000, a peak average molecular weight of 168,000, a number average molecular weight of 37,000 and a polydispersity of 5.7.

Comparative Polymer 3A

A polymer was prepared as described in Polymer Example 3 except that Comparative Monomer 1 was used in place of Monomer Example 1.

Comparative Polymer 3B

A polymer was prepared as described in Polymer Example 3 except that Comparative Monomer 2 was used in place of Monomer Example 1.

Polymer Example 4

Polymer Example 4 was prepared by Suzuki polymerisation as described in WO 00/53656 of the following monomers:

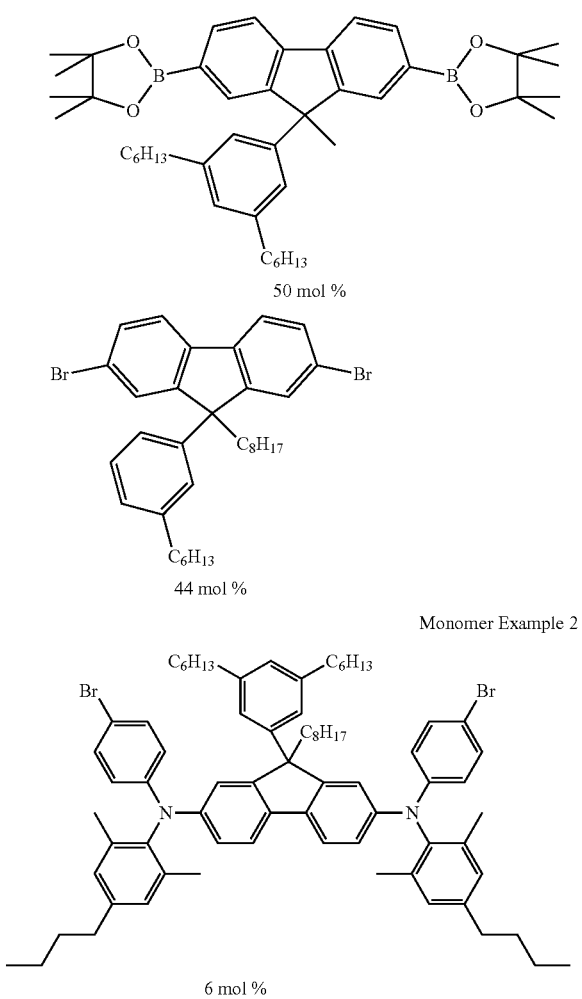

Monomer Example 2

General Device Fabrication Process Devices having the following structure were formed:

ITO/HIL/HTL/EL/Cathode wherein ITO is an indium tin oxide anode, HIL is a hole injection layer, HTL is a hole-transporting layer, and EL is a light-emitting layer.

A substrate carrying ITO was cleaned using UV/Ozone. A hole injection layer was formed by spin-coating an aqueous formulation of a hole-injection material available from Plextronics, Inc. A hole transporting layer was formed to a thickness of 20 nm by spin-coating a hole transporting polymer and crosslinking the hole-transporting polymer by heating. A light-emitting layer was formed by depositing a light-emitting formulation of a light-emitting polymer and an additive polymer (90:10 weight ratio) to a thickness of 75 nm by spin-coating from o-xylene solution. A cathode was formed by evaporation of a first layer of a metal fluoride to a thickness of about 2 nm, a second layer of aluminium to a thickness of about 200 nm and an optional third layer of silver.

The light-emitting polymer was formed by polymerisation of the following monomers by Suzuki polymerisation as described in WO 00/53656:

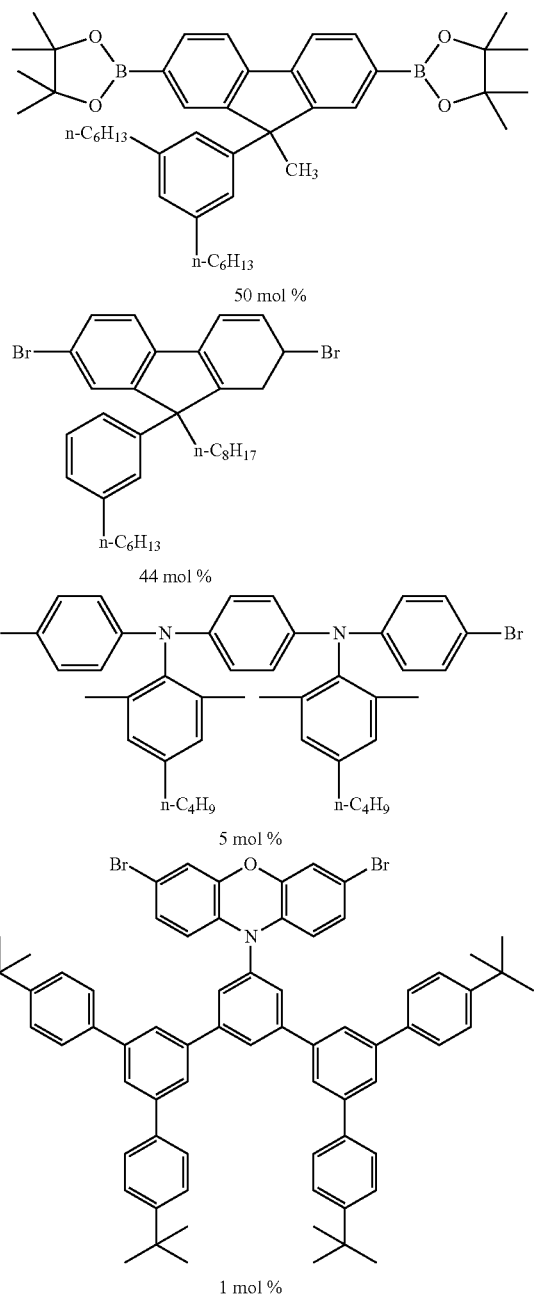

The additive polymer was formed by polymerisation of the following monomers by Suzuki polymerisation as described in WO 00/53656:

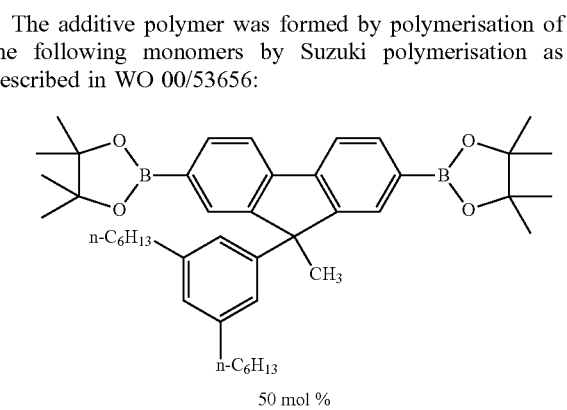

-continued

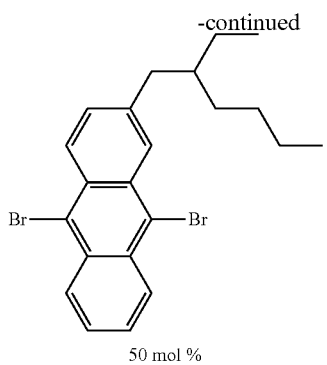

50 mol %

Device Example 1

A device was prepared according to the General Device Fabrication Process wherein the hole transporting layer was formed by spin-coating and crosslinking Polymer Example 1.

Comparative Device 1

A device was prepared according to the General Device Fabrication Process wherein the hole transporting layer was formed by spin-coating and crosslinking Comparative Polymer 1.

Device Example 2

A device was prepared according to the General Device Fabrication Process wherein the hole transporting layer was formed by spin-coating and crosslinking Polymer Example 2.

Comparative Device 2

A device was prepared according to the General Device Fabrication Process wherein the hole transporting layer was formed by spin-coating and crosslinking Comparative Polymer 2.

Figure 2:
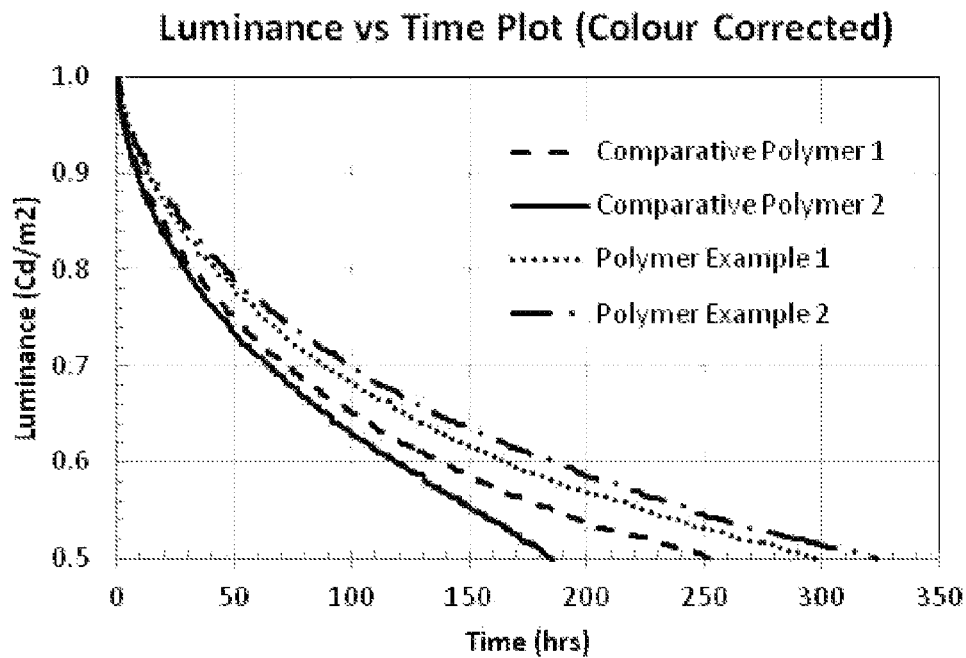
FIG. 2 is a graph of luminance vs. time for exemplary OLEDs containing a hole-transporting layer of a polymer according to an embodiment of the invention and comparative OLEDs.

With reference to FIG. 2, Device Examples 1 and 2 surprisingly both have a longer half-life than Comparative Device 1 and Comparative Device 2 ("half-life" as used herein means the time taken for luminance to fall by 50% from a starting luminance at constant current).

Hole-Only Device Examples

Devices were prepared as described in the general device fabrication process using Polymer Example 1 and Polymer Example 2, except that no light-emitting layer was present, and the cathode was aluminium to reduce injection of electrons as compared to the above device examples.

For the purpose of comparison, the same device was made using Comparative Polymer 1.

Figure 3:
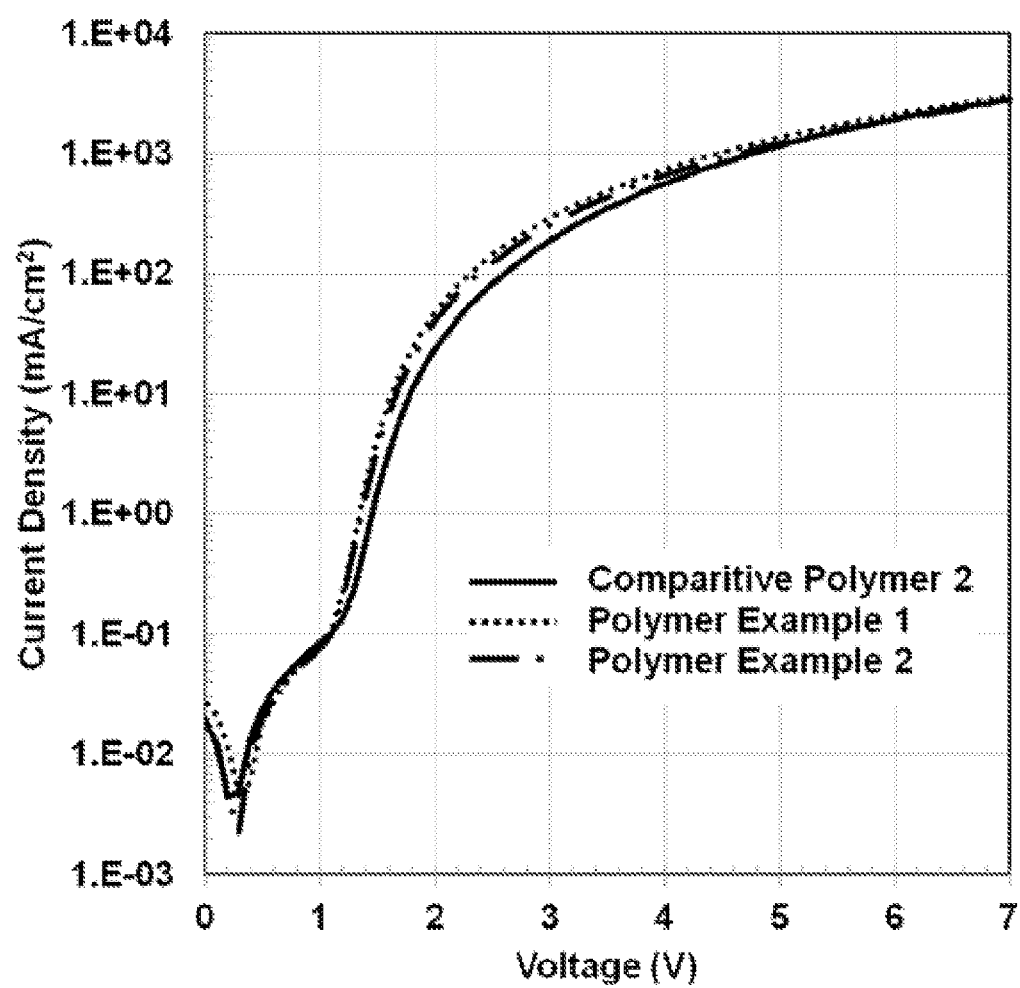
FIG. 3 is a graph of current density vs. voltage for exemplary OLEDs containing a hole-transporting layer of a polymer according to an embodiment of the invention and a comparative OLED.

As shown in FIG. 3, hole-only devices of Polymer Examples 1 and 2 surprisingly have higher hole current than the device formed from Comparative Polymer 2.

Device Example 3

A device was prepared according to the General Device Fabrication Process wherein the hole transporting layer was formed by spin-coating and crosslinking Polymer Example 3.

Comparative Device 3A

A device was prepared as described in Device Example 3 except that Comparative Polymer 3A was used in place of Polymer Example 3.

Comparative Device 3B

A device was prepared as described in Device Example 3 except that Comparative Polymer 3B was used in place of Polymer Example 3.

Figure 4A:
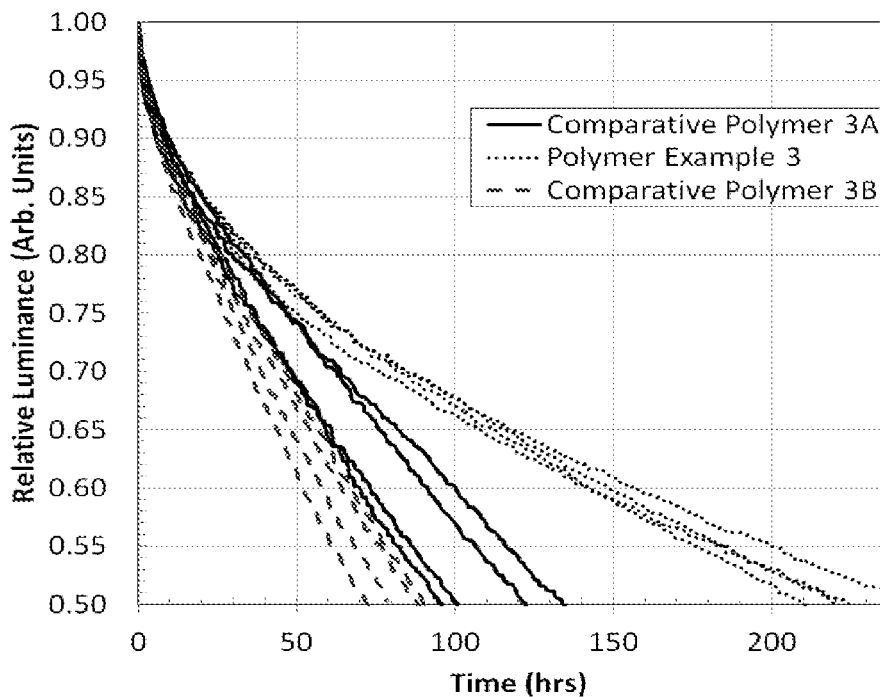
FIG. 4A is a graph of luminance vs. time for an exemplary blue fluorescent OLED containing a hole-transporting layer of a polymer according to an embodiment of the invention and comparative OLEDs.
Figure 4B:
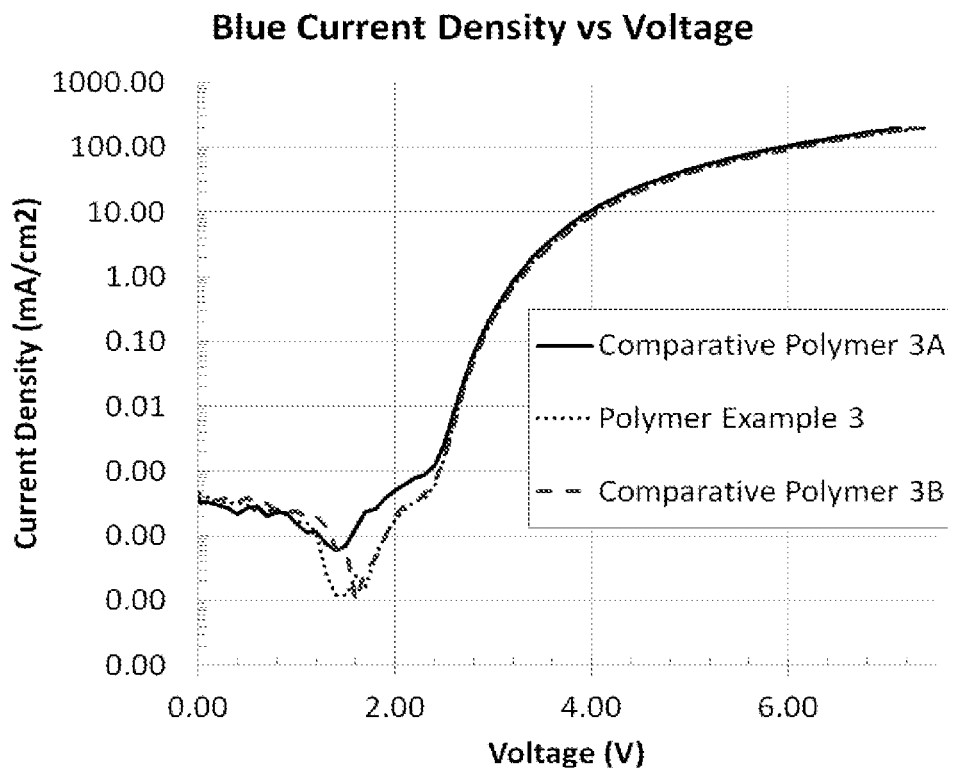
FIG. 4B is a graph of current density vs. voltage for devices of FIG. 4A.

With reference to FIG. 4A, half-life of Device Example 3 is longer than either Comparative Device 3A or 3B. With reference to FIG. 4B, conductivity of Device Example 3 is the same as or similar to those of Comparative Devices 3A and 3B.

Device Example 4

A device was prepared according to the General Device Fabrication Process wherein the hole transporting layer was formed by spin-coating and crosslinking Polymer Example 3, except that the light-emitting layer was formed by spin-coating a polymer host system mixed with 30 weight % of Green Phosphorescent Emitter 1:

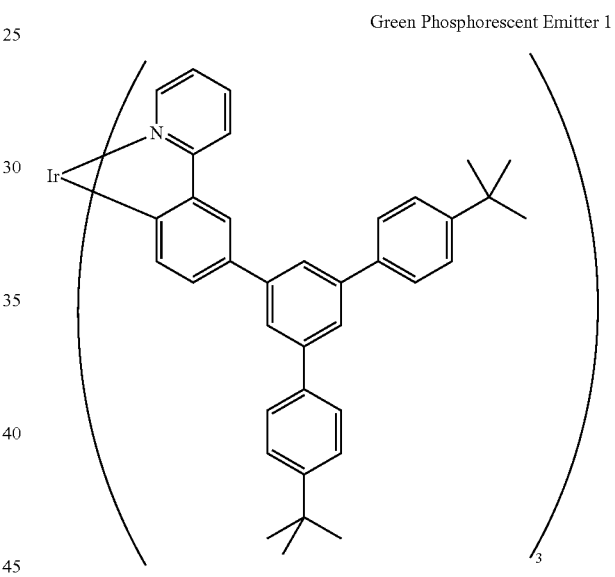

Green Phosphorescent Emitter 1

Comparative Device 4A

A device was prepared as described in Device Example 4 except that Comparative Polymer 3A was used in place of Polymer Example 3.

Comparative Device 4B

A device was prepared as described in Device Example 4 except that Comparative Polymer 3B was used in place of Polymer Example 3.

Figure 5A:
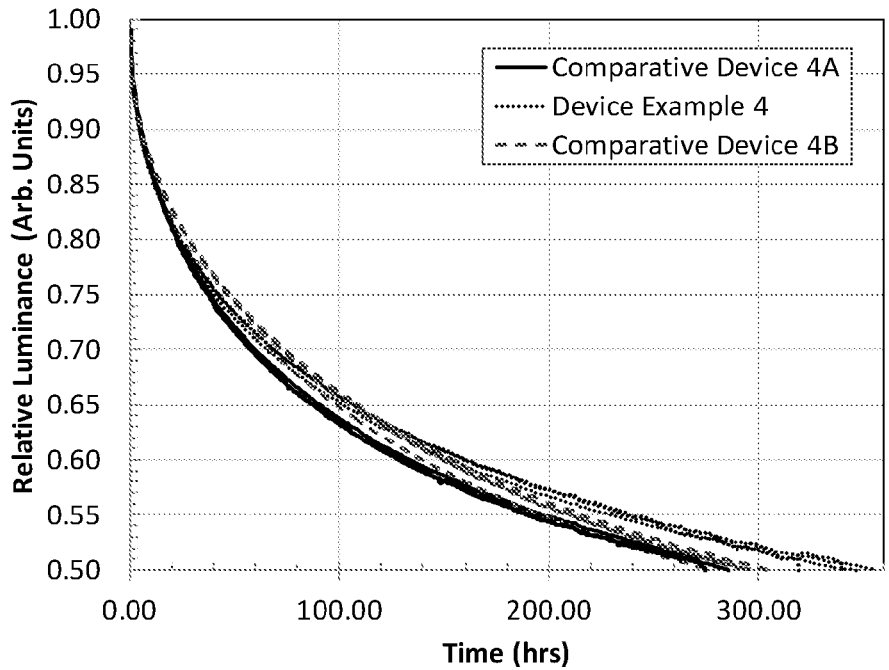
FIG. 5A is a graph of luminance vs. time for an exemplary green phosphorescent OLED containing a hole-transporting layer of a polymer according to an embodiment of the invention and comparative OLEDs.
Figure 5B:
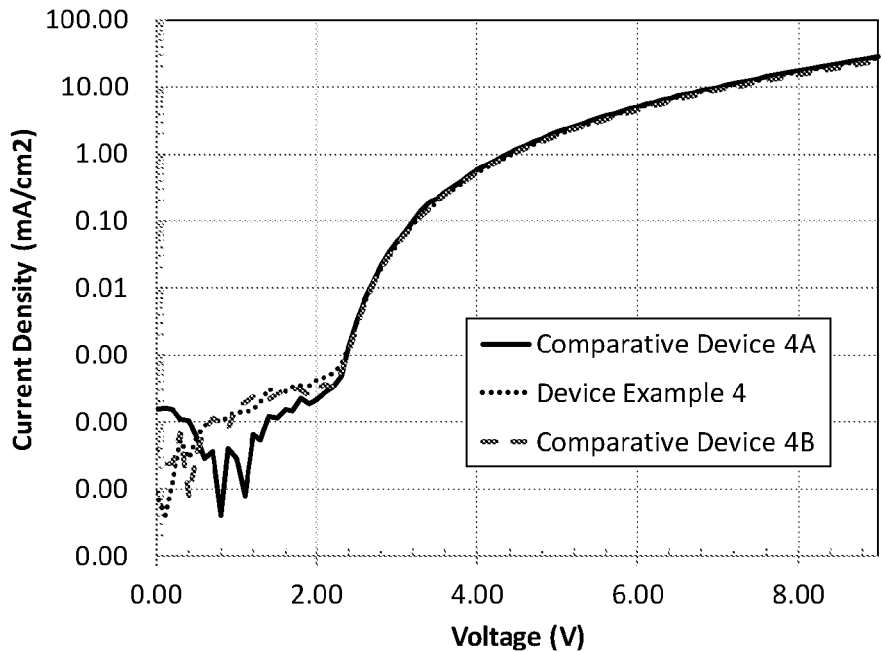
FIG. 5B is a graph of current density vs. voltage for devices of FIG. 5A.

With reference to FIG. 5A, half-life of Device Example 4 is longer than either Comparative Device 4A or 4B. With reference to FIG. 5B, conductivity of Device Example 4 is the same as or similar to those of Comparative Devices 4A and 4B.

Device Example 5

A device having the following structure was formed:
ITO/HIL/HTL/EL/Cathode
wherein ITO is an indium tin oxide anode, HIL is a hole injection layer, HTL is a hole-transporting layer, and EL is a light-emitting layer.

A substrate carrying ITO was cleaned using UV/Ozone. A 35 nm thick hole injection layer was formed by spin-coating an aqueous formulation of a hole-injection material available from Plextronics, Inc. A hole transporting layer was formed to a thickness of 22 nm by spin-coating hole transporting polymer HTL1 and crosslinking the hole-transporting polymer by heating. A light-emitting layer was formed by depositing a light-emitting formulation of Polymer Example 4 and the additive polymer described in the General Device Fabrication process (90:10 weight ratio) to a thickness of 70 nm by spin-coating from o-xylene solution. A cathode was formed by evaporation of a first layer of a metal fluoride to a thickness of about 2 nm, a second layer of aluminium to a thickness of about 200 nm and an optional third layer of silver.

Hole-transporting polymer HTL1 was formed by polymerisation of the following monomers by Suzuki polymerisation as described in WO 00/53656:

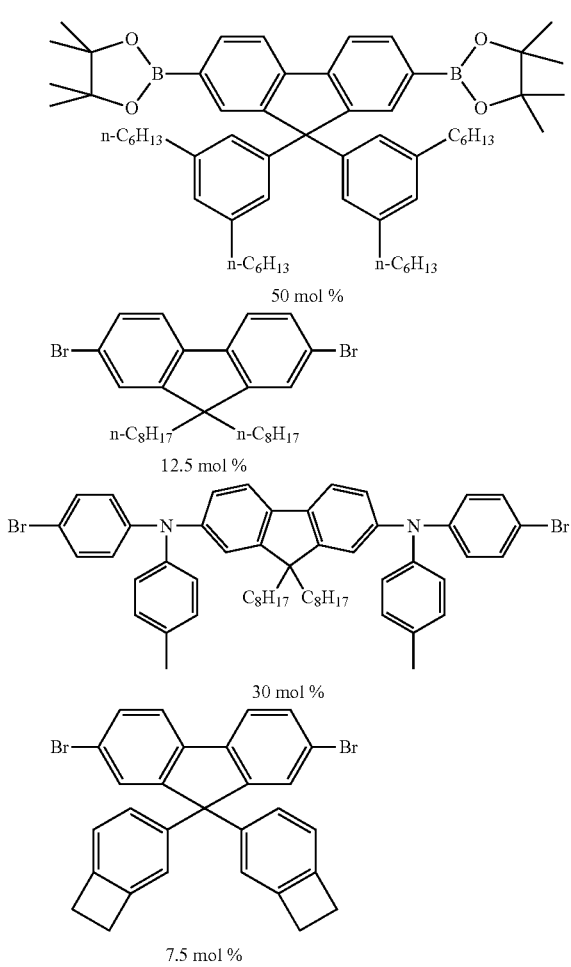

The device produced blue light by emission from Polymer Example 4.

The invention has been described with reference to polymers comprising repeat units of formula (I). Homopolymers or copolymers comprising repeat units of formula (III) may be made and used in devices as described herein with respect to polymers comprising repeat units of formula (I), and $Ar^1$, $Ar^2$, n and m of repeat units of formula (III) may be as described anywhere herein with reference to repeat units of formula (I).

Exemplary repeat units of formula (III) include the following:

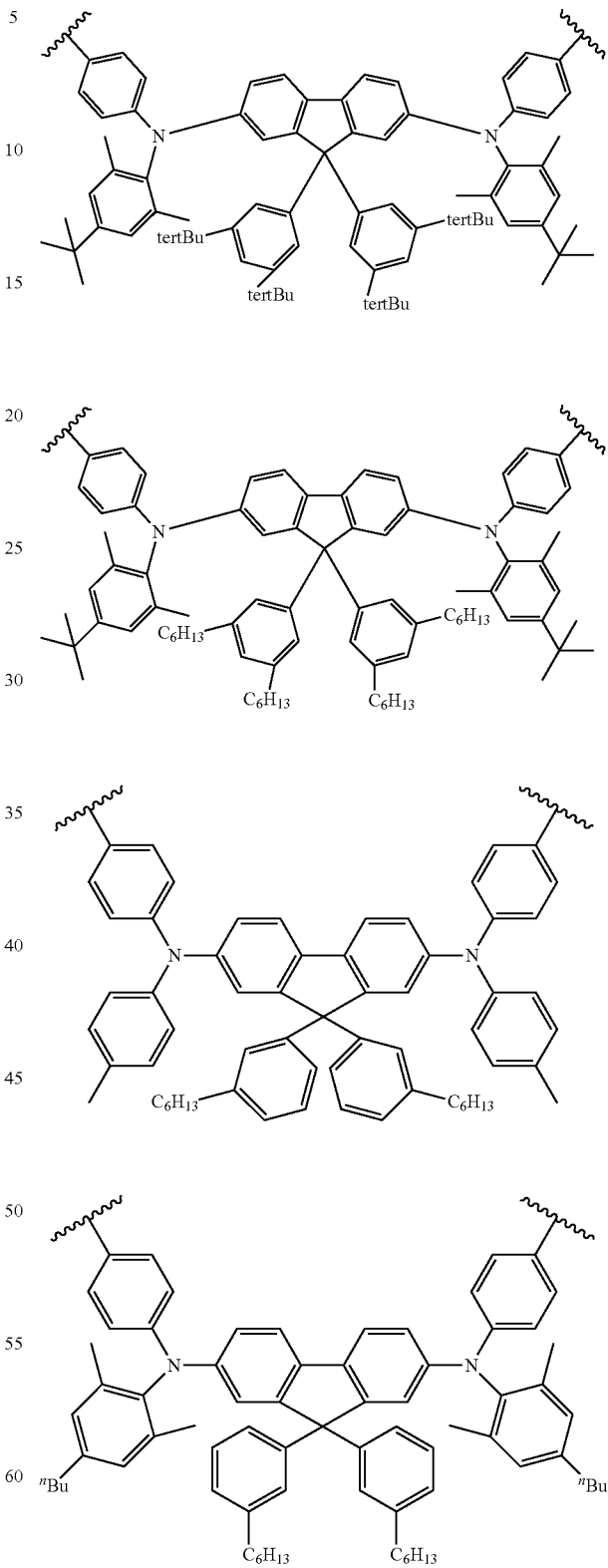

An exemplary synthesis for a monomer that may be used to form a repeat unit of formula (III) is as follows:

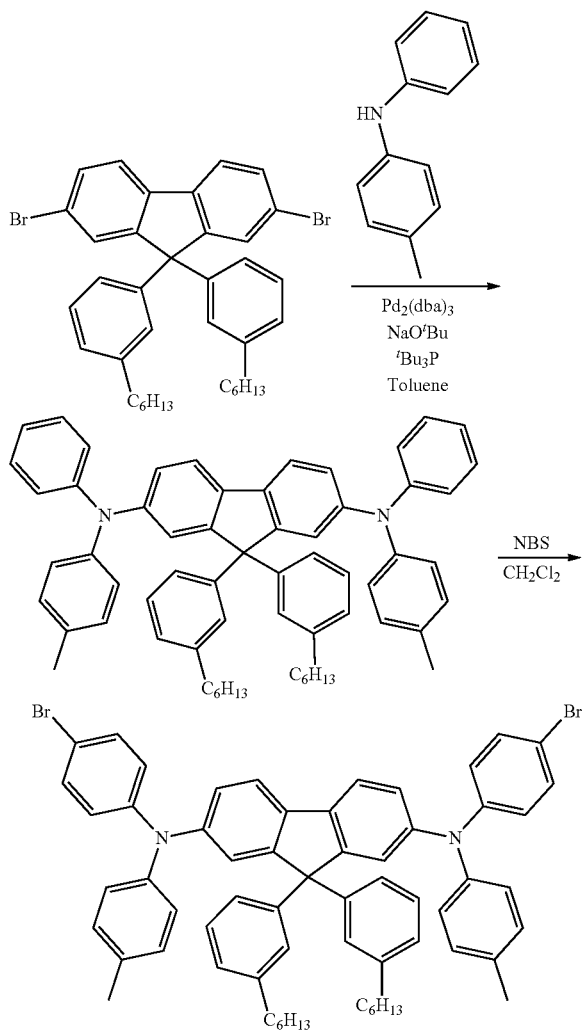

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A polymer comprising one or more unsubstituted or substituted repeat units of formula (I):

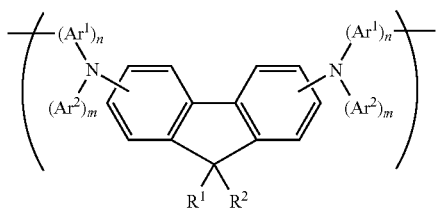

wherein each $Ar^1$ independently represents a substituted or unsubstituted aromatic or heteroaromatic group; each $Ar^2$ independently represents a substituted or unsubstituted aromatic or heteroaromatic group; n and m in each occurrence is at least 1; and $R^1$ and $R^2$ are substituents wherein $R^1$ and $R^2$ are different; wherein $R^1$ is bound to the flourene ring through a $sp^2$-hybridised carbon atom and $R^2$ is bound to the flourene unit through a $sp^3$-hybridized carbon atom.

2. A polymer according to claim 1, wherein $R^2$ is a substituted or unsubstituted, branched, linear, or cyclic alkyl group wherein one or more non-adjacent C atoms may be replaced with O, S, $NR^5$, C=O or —COO—, and one or more H atoms may be replaced with F or D, and $R^5$ is H or a substituent.

3. A polymer according to claim 1, wherein $R^1$ is bound to the fluorene unit through a group —$(Ar^3)_y$, wherein $Ar^3$ in each occurrence is a substituted or unsubstituted aromatic or heteroaromatic group; y is at least 1; and —$(Ar^3)_y$ forms a linear or branched chain of $Ar^3$ groups when y is greater than 2.

4. A polymer according to claim 3, wherein $Ar^3$ in each occurrence is a substituted or unsubstituted phenyl.

5. A polymer according to claim 3 wherein $Ar^3$ is substituted with one or more substituents, selected from F; CN; $NO_2$; $NR^5_2$; a crosslinkable group; and $C_{1-20}$ alkyl wherein one or more non-adjacent C atoms may be replaced with unsubstituted or substituted aryl or heteroaryl, O, S, $NR^5$, C=O or —COO— and wherein one or more H atoms may be replaced with F or D, and $R^5$ is H or a substituent.

6. A polymer according to claim 1 wherein each n is independently 1-3, and wherein each m is independently 1-3.

7. A polymer according to claim 1 wherein each $Ar^1$ and $Ar^2$ is independently an unsubstituted or substituted phenyl.

8. A polymer according to claim 1 wherein at least one $Ar^2$ is substituted with one or more substituents selected from F; CN; $NO_2$; $NR^5_2$; a crosslinkable group; and $C_{1-20}$ alkyl groups wherein one or more non-adjacent C atoms may be replaced with unsubstituted or substituted aryl or heteroaryl, O, S, $NR^5$, C=O or —COO— and wherein one or more H atoms may be replaced with F or D, and $R^5$ is H or a substituent.

9. A polymer according to claim 1 wherein at least one position of at least one $(Ar^2)_m$ that is ortho- to the $Ar^2$—N bond is substituted.

10. A polymer according to claim 1 wherein the polymer comprises a co-repeat unit of formula (IV):

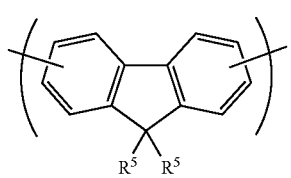

wherein $R^5$ in each occurrence is the same or different and is H or a substituent, and wherein the two groups $R^5$ may be linked to form a ring.

11. A polymer according to claim 1 comprising a repeat unit of formula (Ib):

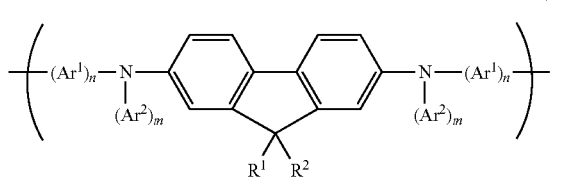

(Ib)

wherein each Ar¹ independently represents a substituted or unsubstituted aromatic or heteroaromatic group; each Ar² independently represents a substituted or unsubstituted aromatic or heteroaromatic group; n and m in each occurrence is at least 1; and R¹ and R² are substituents wherein R¹ and R² are different.

12. A polymer according to claim 1 wherein the repeat unit of formula (I) and/or one or more co-repeat units of the polymer are substituted with at least one crosslinkable group.

13. An organic electronic device comprising a semiconductor layer wherein the semiconductor layer comprises a polymer according to claim 1.

14. An organic electronic device according to claim 13 wherein the device is an organic light-emitting device comprising the semiconductor layer between an anode and a cathode.

15. An organic electronic device according to claim 14 wherein the semiconducting layer is a hole-transporting layer between the anode and a light-emitting layer.

16. A method of forming a polymer according to claim 1 comprising the step of polymerising a monomer of formula (II):

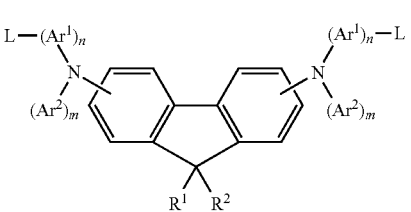

(II)

wherein Ar¹, Ar², R¹, R², n and m are as defined in claim 1, and each L represents a reactive leaving group selected from the group consisting of halogen; boronic acids and esters thereof; and sulfonic acid esters.

17. A method according to claim 16 wherein the polymerisation is carried out in the presence of a metal catalyst.

* * * * *